United States Patent [19]  [11]  4,122,288
Christensen et al.  [45]  Oct. 24, 1978

[54] HYDROLYSIS OF ALKYL SUBSTITUTED DIHALOBENZENE COMPOUNDS

[75] Inventors: Nils J. Christensen, Palatine; Joseph Levy, Northbrook, both of Ill.

[73] Assignee: UOP Inc., Des Plaines, Ill.

[21] Appl. No.: 852,018

[22] Filed: Nov. 16, 1977

[51] Int. Cl.$^2$ ............................................. C07C 39/26
[52] U.S. Cl. ................................................... 568/775
[58] Field of Search ........................... 260/623 R, 629

[56] References Cited

U.S. PATENT DOCUMENTS 2,934,569  4/1960  Kuehlewind, Jr. .............. 260/623 R
2,950,325  8/1960  Britton et al. ................... 260/623 R Primary Examiner—James O. Thomas, Jr.
Assistant Examiner—Werren B. Lone
Attorney, Agent, or Firm—James R. Hoatson, Jr.; Raymond H. Nelson; William H. Page, II

[57] ABSTRACT

Alkyl substituted 1,2-halofluorinated aromatic compounds may be subjected to hydrolysis to form an alkyl substituted o-fluorophenol by treating said compound with water in the presence of a relatively mildly basic compound such as the salt of a strong base and a weak acid at hydrolysis conditions to form the desired compound.

6 Claims, No Drawings

HYDROLYSIS OF ALKYL SUBSTITUTED DIHALOBENZENE COMPOUNDS

The invention herein described was made in the course of or under a contract or subcontract thereunder with the United States Air Force.

BACKGROUND OF THE INVENTION

With the advent of aircraft which are able to fly at relatively high speeds greater than Mach 1 plus the ability to climb to high altitudes, it is necessary to provide an oxygen system which will perform under these relatively harsh conditions. This is especially true in the case of military aircraft which must possess the ability to fly higher, faster, longer and with greater maneuverability than other aircraft. In supplying an oxygen system for the cockpit of military aircraft, it is necessary to have a system which will perform in an adequate manner and which will be relatively light in weight. Another criteria is that the system be relatively small in size inasmuch as the cockpit area, especially in pursuit or fighter aircraft, is relatively small. One method of supplying oxygen to the personnel on the aircraft is to store oxygen as a liquid. One advantage in using such a system is that liquid oxygen does not require a high pressure tank and the ratio of system volume and weight versus the usable material could be drastically reduced. However, the disadvantage to the use of such a system is that expensive equipment is required on the ground in order to handle the problems of handling the cryogenic liquid.

As an alternative to using the relatively expensive liquid oxygen system, it has been found possible to concentrate oxygen use of the air and provide it to the aircraft crew members via certain metal chelates. One such metal chelate which has been found to be effective in the generation of oxygen from air is cobalt bis(3-fluorosalicylaldehyde)ethylenediimine which is known as fluomine. This cobalt chelate compound can reversibly bind oxygen and generate it by absorbing the oxygen at low temperatures and desorbing it at higher temperatures. For example, fluomine will absorb oxygen at a maximum rate between 80° and 100° F. while the desorption of the oxygen will take place above about 180° F. at relatively low pressures. A precursor to the aforementioned fluomine comprises 3-fluorosalicylaldehyde. This compound is prepared in a series of steps utilizing o-fluorophenol as the starting material.

The o-fluorophenol which is used as the starting material for the preparation of fluomine usually was obtained as a by-product which resulted from the production of p-fluorophenol. In forming this product p-nitrochlorobenzene which was contaminated with o-nitrochlorobenzene was treated to obtain the isomeric fluorophenols, the yield of the isomeric fluorophenols from the isomeric nitrochlorobenzenes usually ranged from 45% to 80%. Other direct ways of obtaining the desired product, namely, o-fluorophenol, which started with o-nitrochlorobenzene, are elaborate in nature utilizing such compounds as potassium fluoride, dimethylsulfoxide, nitric acid, sulfuric acid, etc. However, when utilizing these compounds it is necessary to use relatively expensive and elaborate equipment and, therefore, it is not economically feasible to obtain the desired product when utilizing this process. As will hereinafter be set forth in greater detail, in a process for producing o-fluorophenol starting with fluorobenzene which is relatively inexpensive, it is possible to alkylate this compound, brominate the alkyl fluorobenzene to form an alkyl substituted 1,2-bromofluorobenzene compound, and, in the process of the present invention, hydrolyze this compound to form an alkyl substituted o-fluorophenol. This latter compound may then be treated by dealkylation means to form a desired o-fluorophenol.

This invention relates to a process for the hydrolysis of an alkyl substituted 1,2-halofluorobenzene compound. More specifically, the invention is concerned with a process for the hydrolysis of an alkyl substituted 1,2-dihalobenzene compound, said compound containing two dissimilar halogen substituents of which one is fluorine to form the corresponding ortho-fluorophenol. This latter compound may then be dealkylated to form o-fluorophenol which is utilized as a starting material in preparing compounds which are useful for generating oxygen. In order to set forth a process whereby the final product such as fluomine is prepared in an economical manner, it is necessary that all steps which are required for the production of the product also be operated in an economical manner. Inasmuch as the starting material for preparing fluomine which is also known as cobalt bis(3-fluorosalicylaldehyde)ethylenediimine is o-fluorophenol, it is necessary that this material cost as little as possible. The steps of synthesizing this starting material are relatively complex inasmuch as fluorobenzene, the basic material, must be subjected to a series of reactions in order to obtain the desired product.

It is therefore an object of this invention to provide a process for the hydrolysis of an alkyl substituted 1,2-halofluorobenzene compound.

A further object of this invention is to provide an improved process for the hydrolysis of an alkyl substituted 1,2-halofluorobenzene compound which is an intermediate in a process for preparing o-fluorinated phenols.

In one aspect an embodiment of this invention resides in a process for the hydrolysis of an alkyl substituted 1,2-halofluorobenzene compound which comprises treating said compound with water and a basic compound at hydrolysis conditions, and recovering the resultant hydrolyzed compound.

A specific embodiment of this invention resides in a process for the hydrolysis of an alkyl substituted 1,2-halofluorobenzene which comprises treating 2-bromo-4-t-butylfluorobenzene with water in the presence of sodium acetate at a temperature in the range of from about 100° to about 300° C. and a pressure in the range of from about atmospheric to about 2000 pounds per square inch, and recovering the desired 5-t-butyl-2-fluorophenol.

Other objects and embodiments will be found in the following detailed description of the present invention.

As hereinbefore set forth the present invention is concerned with the process for the hydrolysis of alkyl substituted 1,2-dihalobenzene compounds which contain two dissimilar halogen substituents one of which is fluorine. The starting material for the process of this invention may be obtained from any source known in the art. For example, one method of approach for obtaining the starting materials may comprise alkylating a halobenzene such as fluorobenzene with an olefin or an alkyl halide as the alkylating agent to form a bulky tertiary or secondary alkyl group in the para position. The alkylation of the fluorobenzene is preferably effected at temperatures ranging from about 0° up to about 50° C. or more in the presence of a conventional acidic alkylation catalyst. Examples of alkylating agents which may be employed to form the desired product will preferably include olefins or alkyl halides containing from about 4 to 10 carbon atoms such as isobutylene, isopentene, isohexene, isoheptene, isooctene, isononene, isodecyl, t-butylchloride, t-butylbromide, 2-chloro-1-methylbutane, 2-bromo-2-methylbutane, 2-chloro-2-methylpentane, 2-bromo-2-methylpentane, 3-bromo-3-methylpentane, 2-chloro-2-methylhexane, 3-bromo-3-methylhexane, 3-chloro-3-methylheptane, 4-bromo-4-methylheptane, etc.

The thus formed 4-alkylfluorobenzene may then be brominated at a temperature within the range of from about 0° to about 75° C. in the presence of a catalyst which may include iodine, iron, etc., to form the corresponding 4-alkyl-2-bromofluorobenzene. Thereafter the alkyl substituted dihalobenzene compound which contains both a bromo and a fluoro substituent on adjacent carbon atoms of the benzene ring is subjected to hydrolysis in a manner hereinafter set forth in greater detail.

The hydrolysis of the alkyl substituted 1,2-halofluorobenzene compound is effected by treating the compound with water in the presence of a relatively mildly basic compound at hydrolysis conditions. The hydrolysis conditions which are employed in the process of this invention will include temperatures ranging from about 100° to about 300° C. and pressures ranging from atmospheric to about 2000 pounds per square inch. The mildly basic compound which is utilized will preferably comprise the salt of a strong base and a weak acid. Some examples of these basic compounds which may be employed will include the salts of a strong base such as an alkali metal hydroxide and a weak organic or inorganic acid such as sodium formate, potassium formate, lithium formate, sodium acetate, potassium acetate, lithium acetate, sodium propionate, potassium propionate, lithium propionate, sodium butyrate, potassium butyrate, lithium butyrate, sodium phosphate, potassium phosphate, lithium phosphate, sodium bisulfite, potassium bisulfite, lithium bisulfite, sodium sulfide, potassium sulfide, lithium sulfide, etc., sodium acetate being the preferred salt. It is to be understood that the aforementioned salts are only representative of the type of mildly basic compound which may be employed, and that the present invention is not necessarily limited thereto. By utilizing the aforementioned salts in the treatment of the alkyl substituted halogenated benzene compound with water, it is possible to displace the bromine followed by hydrolysis in situ to the phenol without going through a benzyne intermediate which would be expected if a strong base were used in the hydrolysis. This is important inasmuch as the product which results from the process of this invention will retain its original configuration inasmuch as the displacement-hydrolysis of the benzene compound will occur without isomerization via benzyne formation, which would destroy the possibility of obtaining the desired end product, namely an o-halophenol such as o-fluorophenol. An additional advantage which is found when utilizing this type of hydrolysis is that the materials which are utilized are relatively inexpensive and furthermore the process may be carried out using relatively inexpensive equipment.

In addition, it is also contemplated within the scope of this invention that a copper compound may also be present in the reaction mixture, as a catalyst for the reaction, said copper compounds including copper oxides, halides, etc. In addition to the basic compound, water and copper compound, it is also possible, within the parameters of the process, to employ aprotic or dipolar solvents such as sulfolane, N-methyl-2-pyrrolidone, etc., to facilitate the reaction. In like manner, it is also considered within the scope of this invention that quaternary salts such as tetramethylammonium chloride, tetraethylammonium chloride, tetrapropylammonium chloride, tetrabutylammonium chloride, benzyltrimethylammonium chloride, benzyltriethylammonium bromide, benzyltripropylammonium chloride, benzyltributylammonium bromide, tetramethylphosphonium chloride, tetraethylphosphonium chloride, tetrapropylphosphonium bromide, tetrabutylphosphonium chloride, benzyltrimethylphosphonium chloride, benzyltriethylphosphonium bromide, benzyltributylphosphonium chloride, etc., may also be used as a phase transfer catalyst, although not necessarily with equivalent results.

The process of the present invention may be effected in any suitable manner and may comprise either a batch or continuous type of operation. For example, when a batch type operation is employed a quantity of the alkyl substituted 1,2-halofluorobenzene compound containing two dissimilar halogen constituents are placed in an appropriate apparatus which may comprise a flask or an autoclave of the rotating or mixing type. In addition, water is also placed in the apparatus along with the basic compound such as sodium acetate and, if so desired, a copper compound and/or a quaternary salt of the type hereinbefore described. In addition, if a solvent of the type hereinbefore described is to be employed in the system it is also added to the apparatus which is thereafter heated to the desired operating temperature in the range hereinbefore set forth. Likewise, if superatmospheric pressures are to be employed the apparatus which in this instance comprises an autoclave is sealed and the desired operating pressure is obtained either by the introduction of a substantially inert gas such as nitrogen into the reaction zone or the autogeneous pressure of the reaction. Upon completion of the desired residence time which may range from about 0.5 up to about 10 hours or more in duration, heating is discontinued and the apparatus and contents thereof are allowed to return to room temperature. Any superatmospheric pressure, if present, is discharged and the reaction mixture is recovered from the apparatus. Thereafter the reaction mixture is subjected to conventional means of product recovery such as separation of the aqueous layer from the organic layer, drying of the organic layer followed by fractional distillation whereby the desired product comprising the alkyl substituted halophenol is separated from any unreacted starting material and/or side products which may have been formed during the reaction and recovered.

It is also contemplated within the scope of this invention that the hydrolysis process may be accomplished by utilizing a continuous manner of operation. When such a type of operation is employed the alkyl substituted halobenzene compound is continuously charged to a reaction vessel which is maintained at the proper operating conditions of temperature and pressure. In addition, water and the basic compound are also continuously charged to the reactor along with the solvent and catalyst, in the event that the latter two components of the latter mixture are to be used, in a continuous manner. If so desired, one or more of the components of the reaction mixture may be admixed prior to entry into said reactor and the resulting mixture charged thereto in a single stream. After passage of the desired residence time the reactor effluent is continuously withdrawn and subjected to conventional means of separation whereby any unreacted starting materials may be separated and recycled to the reaction zone to form a portion of the feedstock while the desired alkyl substituted halophenol may be recovered.

The following examples are given for purposes of illustrating the process of this invention. However, it is to be understood that these examples are given merely for purposes of illustration and that said invention is not necessarily limited thereto.

EXAMPLE I

In this example 20.0 grams (0.08 mole) of 4-t-butyl-2-bromofluorobenzene, 180 grams of water, 26.2 grams (0.32 mole) of sodium acetate, and 1.0 gram of cuprous oxide were placed in a 300 ml magnetically stirred autoclave. The autoclave was sealed and heated to a temperature of about 250° C. under an initial 50 psi blanket of nitrogen, the total pressure rising to about 600 psig during the reaction period. The reaction vessel was maintained at this temperature for a period of about 8.0 hours, at the end of which time heating was discontinued and the autoclave was returned to room temperature. The excess pressure was discharged, the contents were removed from the autoclave and the autoclave was rinsed with toluene to remove any residuals. The aqueous layer was extracted once with toluene to remove any occluded organics, mixed with the organic layer and the bulk of the toluene was stripped off on a distillation column under atmospheric conditions. Analysis by means of a gas liquid chromatograph disclosed that there had been a 95% conversion of the starting material with a 75% selectivity to 5-t-butyl-2-fluorophenol, the reaction conversion and selectivity being verified by means of fractional distillation of the product and gas liquid chromatographic analyses of the distillate cuts.

EXAMPLE II

In this example the use of a solvent was illustrated in which 20.0 grams (0.08 mole) of 4-t-butyl-2-bromofluorobenzene, 40 grams of N-methyl-2-pyrrolidone, 150 grams of water, 26.2 grams of sodium acetate, and 1 gram of cuprous oxide were placed in an autoclave which was thereafter sealed and heated to a temperature of about 250° C. under an initial 50 psi blanket of nitrogen. The reaction was effected at operating conditions which included a temperature of about 250° C. and a pressure of about 560 psi for a period of about 6.6 hours. At the end of this period heating was discontinued and the autoclave allowed to return to room temperature. The excess pressure was discharged, the autoclave was opened and the contents were removed therefrom. The autoclave was rinsed with toluene which was added to the mixture. Following this the aqueous layer was separated from the organic layer and the former was extracted with toluene to remove any occluded organic material. The toluene extract was combined with the organic layer and the bulk of the toluene was stripped off in a manner similar to that set forth in the example above. Analysis of the product by means of a gas liquid chromatograph showed that there had been a 95% conversion of the starting material with a 74% selectivity to 5-t-butyl-2-fluorophenol. Fractional distillation of this product followed by gas liquid chromatographic analyses also confirmed the conversion and selectivity to the desired product.

EXAMPLE III

In a manner similar to that set forth in the above examples, 2-bromo-4-sec-amylfluorobenzene along with water, sodium bisulfite, and a solvent comprising sulfolane may be placed in an autoclave which is then sealed and charged with 50 psi of nitrogen. The autoclave may then be heated to a temperature of about 250° C. and maintained thereat for a period of about 8 hours while maintaining the contents of the autoclave in a constant state of agitation. At the end of the 8 hour period heating may be discontinued and the autoclave allowed to return to room temperature. Upon returning to room temperature the excess pressure may be discharged, the autoclave opened and the contents removed therefrom. After treatment of the reaction mixture in a manner similar to that hereinbefore set forth the presence of the desired 5-sec-amyl-2-fluorophenol may be verified by subjecting the mixture to fractionation and analyses by gas liquid chromatography.

We claim as our invention:

1. A process for the preparation of 5-t-butyl-2-fluorophenol which comprises treating 4-t-butyl-2-bromofluorobenzene with water and a salt of a strong base and a weak acid at a temperature of from about 100° C. to about 300° C., a pressure of from about atmospheric to about 2000 pounds per square inch and a time period of from about 0.5 to about 10 hours.

2. The process as set forth in claim 1 further characterized in that said process is effected in the presence of a catalyst comprising a copper compound.

3. The process as set forth in claim 1 in which said salt is sodium acetate.

4. The process as set forth in claim 1 in which said salt is sodium bisulfite.

5. The process as set forth in claim 1 in which said salt is sodium sulfide.

6. The process as set forth in claim 2 in which said catalyst comprises cuprous oxide.

* * * * *